United States Patent [19]
Barr et al.

[11] Patent Number: 5,998,131
[45] Date of Patent: Dec. 7, 1999

[54] SCREENING METHODS FOR THE IDENTIFICATION OF COMPOUNDS CAPABLE OF ABROGATING BAK-BHRF-1 PROTEIN INTERACTIONS

[75] Inventors: Philip J. Barr, Berkeley; Michael C. Kiefer, Clayton, both of Calif.

[73] Assignee: LXR Biotechnology, Inc., Richmond, Calif.

[21] Appl. No.: 08/944,530

[22] Filed: Oct. 7, 1997

Related U.S. Application Data

[62] Continuation of application No. 08/426,529, Apr. 20, 1995, abandoned, which is a continuation-in-part of application No. 08/320,157, Oct. 7, 1994, which is a continuation-in-part of application No. 08/160,067, filed as application No. PCT/US94/13930, Nov. 30, 1994, abandoned.

[51] Int. Cl.$^6$ .......................... C12Q 1/70; A61K 39/245; A61K 39/23
[52] U.S. Cl. ........................ 435/5; 424/230.1; 424/233.1
[58] Field of Search .......................... 435/4, 5, 7.1, 69.1, 435/71.1, 172.3; 530/350; 436/501

[56] References Cited

FOREIGN PATENT DOCUMENTS

| WO 93/04169 | 3/1993 | WIPO . |
| WO 94/00572 | 1/1994 | WIPO . |
| WO 95/00160 | 1/1995 | WIPO . |
| WO 95/00642 | 1/1995 | WIPO . |
| WO 95/05738 | 3/1995 | WIPO . |
| WO 95/05750 | 3/1995 | WIPO . |
| WO 95/15084 | 6/1995 | WIPO . |

OTHER PUBLICATIONS

Ameisen et al., "Cell dysfunction and depletion in AIDS: The programmed cell death hypothesis" *Immunol. Today* (1991) 12: 102–105.

Barr, "Expression of foreign genes in yeast" *Transgenesis* (1992) pp. 55–79.

Boise et al., "bcl–x, a bcl–2–related gene that functions as a dominant regulator of apoptotic cell death" *Cell* (1993) 74: 597–608.

Chen–Levy et al., "The bcl–2 candidate proto–oncogene product is a 24–kilodalton integral–membrane protein highly expressed in lymphoid cell lines and lymphomas carrying the t(14;18) translocation" *Mol. Cell Biol.* (1989) 9: 701–710.

Chittenden et al., "Unduction of apoptosis by the Bcl–2 homologue Bak" *Nature* (1995) 347: 733–736.

Clearly et al., "Cloning and structural analysis of cDNAs for bcl–2 and a hybrid bcl–2/immunoglobin transcript resulting from the t(14;18) translocation" *Cell* (1986) 47: 19–28.

Cohen et al., "Apoptosis and programmed cell death in immunity" *Ann. Rev. Immunol.* (1992) 10: 267–293.

Duke et al., "IL–2 addiction: Withdrawal of growth factor activates a suide program in dependent T Cells" *Lymphokine Res.* (1986) 5: 289–299.

Edgington, "Looking death in the eye: Apoptosis and cancer research" *Biotech.* (1993).

Farrow et al., "Cloning of a bcl–2 homologue by interaction with adenovirus E1B 19K" *Nature* (1995) 374: 731–733.

Feinberg et al., "A technique for radiolabeling DNA restriction endonuclease to high specific actiity" *Anal. BIochem* (1984) 137: 266–267.

Gerchenson et al., "Apoptosis: A different type of cell death" *FASEB J.* (1992) 6: 2450–2455.

Hickish et al., "Ultrastructural localization of BHRF1: An Epstein–Barr virus gene product which has homology with bcl–2" *Cancer Research* (1994) 54: 2808–2811.

Hockenbery et al., "Bcl–2 functions in an antioxidant pathway to prevent apoptosis" *Cell* (1993) 75: 241–251.

(List continued on next page.)

Primary Examiner—Laurie Scheiner
Assistant Examiner—Jeffrey S. Parkin
Attorney, Agent, or Firm—Sheridan Ross P.C.

[57] ABSTRACT

The present invention provides methods for screening potential anti-viral therapeutic agents by monitoring their ability to disrupt the interaction between the BAK protein and a viral protein.

6 Claims, 8 Drawing Sheets

1) *In vitro* co-translated proteins
2) Proteins bound to anti-FLAG agarose

OTHER PUBLICATIONS

Jacobson et al., "Bcl–2 blocks apoptosis in cells lacking mitochondrial DNA" *Nature* (1993) 361: 365–369.

Kanter et al., "Epidermal growth factor and tumor promoters prevent DNA fragmentation by different mechanisms" *Biochem. Biophys. Res. Commun.* (1984) 118: 392–399.

Kiefer et al., "Modulation of apoptosis by the widly distributed Bcl–2 homologue Bak" *Nature* (1995) 374: 736–739.

Kiefer et al., "Molecular cloning of a new human insulin–ike growth factor binding protein" *Biochem. Biophys. Res. Commun.* (1991) 176: 219–225.

Kruman et al., "Apoptosis of Murine BW 5147 thymoma cells induced by dexamethasone and γ–irradiation" *J. Cell. Physiol.* (1991) 148: 267–273.

Lehrach et al., "RNA molecular weight determinations by gel electrophoresis under denaturing conditions, a critical reexamination" *Biochem.* (1977) 16: 4743–4751.

McDonnell et al., "Progression from lymphoid hyperplasia to high–grade malignant lymphoma in mice transgenic for the t(14;18)" *Nature* (1991) 349: 254–256.

Monaghen et al., "Ultrastructural localization of bcl–2 protein" *J. Histochem. Cytochem.* (1992) 40: 1819–1825.

Oltvai et al., "Bcl–2 heterodimerizes in vivo with a conserved homolog, Bax, that accelerates programmed cell death" *Cell* (1993) 74: 609–619.

Sanger et al., "DNA sequencing with chain–terminating inhibitors" *Proc. Natl. Acad. Sci. USA* (1977) 74: 5463–5467.

Sentman et al., "Bcl–2 inhibits multiple forms of apoptosis but not negative selection in thymocytes" *Cell* (1991) 67: 879–888.

Sheppard et al, "The relationship between AIDS and immunologic intolerance" *J. AIDS* (1992) 5: 143–147.

Strasser, "Bcl–2 transgene inhibits T cell death and perturbs thymic self–censorship" *Cell* (1991) 67: 889–899.

Tarodi et al., "Epstein–Barr virus BHRF1 protein protects against cell death induced by DNA–damaging agents and heterologous viral infection" *Virology* (1994) 201: 404–407.

Thomas, "Hybridization of denatured RNA and small DNA fragments transferred to nitrocellulose" *Proc. Natl. Acad. Sci. USA* (1980) 77: 5201–5205.

Tomei et al., "Inhibition of radiation–induced apoptosis in vitro by tumor promoters" *Biochem. BIophys. Res. Commun.* (1988) 155: 324–331.

Tsujimoto et al., "Cloning of the chromosome breakpoint of neoplastic B cells with the t(14;18) chromosome translocation" *Science* (1984) 226: 1097–1099.

Veis et al., "Bcl–2–deficient mice demonstrate fulminant lymphoid apoptosis, polycystic kidneys, and hypopigmented haid" *Cell* (1993) 75: 229–240.

Williams set al., "Molecular regulation of apoptosis: genetic controls on cell death" *Cell* (1993) 74: 777–779.

Wyllie, "Glucocorticoid–induced thymocyte apoptosis is associated with endogenous endonuclease activation" *Nature* (1980) 284: 555–556.

Zapf et al., "Isolation from adult human serum of four insulin–like growth factor (IGF) binding proteins and molecular cloning of one of them that is increased by IGF I administration and in extrapancreatic tumor hypoglycemia" *J. Biol. Chem.* (1990) 265: 14892–14898.

Zhu et al., "Systemic gene expression after intravenous DNA delivery into adult mice" *Science* (1993) 261: 209–211.

Cheng et al., "A Bcl–2 homolog encoded by Kaposi sarcoma–associated virus, human herpesvirus 8, inhibits apoptosis but does not heterodimerize with Bax or Bak" *Proc. Natl. Acad. Sci. USA* (1977) 94: 690–694.

D'Sa–Eipper et al., "*bfl*–1, a *bcl*–2 homologue, suppresses p53–induced apoptosis and exhibits potent cooperative transforming activity" *Cancer Research* (1996) 56 (17): 3879–3882.

Henderson et al., "Epstein–Barr virus–coded BHRF1 protein, a viral homologue of Bcl–2, protects human B cells from programmed cell death" *Proc. Natl. Acad. Sci. USA* (1993) 90(18): 8479–8483.

Lewin, R., "When does homology mean something else?" *Science* (1987) 237: 1570.

Murray et al., "BCL–2 but not its Epstein–Barr virus–encoded homologue, BHRF1, is commonly expressed in post–transplantation lymphoproliferative disorders" *Blood* (1996) 87(2): 706–711.

Nava et al., "Herpesvirus saimiri encodes a functional homolog of the human *bcl*–2 oncogene" *J. of Virology* (1997) 71(5): 4118–4122.

Nicholas et al., "A single 13–kilobase divergent locus in the kaposi sarcoma–associated herpesvirus (human herpesvirus 8) genome contains nine open reading frames that are homologous to or related to cellular proteins" *J. of VIrology* (1997) 71(3): 1963–1974.

Reeck et al., "'Homology' in proteins and nucleic acids: A terminology muddle and a way out of it" *Cell* (1987) 50: 667.

Sarid et al., "Kaposi's sarcoma–associated herpesvirus encodes a functional Bcl–2 homologue" *Nature Medicine* (1997) 3(3): 293–298.

Smith, C.A., "A novel viral homologue of Bcl–2 and Ced–9" *Trends in Cell Biology* (1995) 5(9):344.

Theodorakis et al., "Unmasking of a proliferation–restraining activity of the anit–apoptosis protein EBV BHRF1" *Oncogene* (1996) 12(8): 1707–1713.

Virgin IV, et al., "Complete sequence and genomic analysis of murine gammaherpesvirus 68" *J. of Virology* (1997) 71(8): 5894–5904.

Wylie, "Glucocorticoid–induced thymocyte apoptosis is associated with endogenous endonuclease activation" *Nature* (1980) 284:555–556.

Sheppard et al., "The relathioship between AIDS and immunologic intolerance" *J. AIDS* (1992) 5:143–147.

Gerschenson et al., "Apoptosis: A different type of cell death" *FASEB J.* (1992) 6:2450–2455.

Cohen et al. "Apoptosis and programmed cell death in immunity" *Ann. Rev. Immunol.* (1992) 10:267–293.

Cleary et al., "Cloning and structural analysis of cDNAs for *bcl*–2 and a hybrid *bcl*–2/immunoglobin transcript resulting from the t(14;18) translocation" *Cell* (1986) 47:19–28.

Strasser, "*bcl*–2 transgene inhibits T cell death and perturbs thymic self–censorship" *Cell* (1991) 67:889–899.

Williams et al., "Molecular regulation of apoptosis: genetic controls on cell death" *Cell* (1993) 74:777–779.

Veis et al., "Bcl–2–deficient mice4 demonstrate fulminant lymphoid apoptosis, polycystic kidneys, and hypopigmented hair" *Cell* (1993) 75:229–240.

Chen–Levy et al., "The *bcl*–2 candidate proto–oncogene product is a 24–kilodalton integral–membrane protein highly expressed in lymphoid cell lines and lymphomas carrying the t(14;18) translocation" *Mol. Cell. Biol.* (1989) 9:701–710.

Jacobson et al., "Bcl–2 blocks apoptosis in cells lacking mitochondrial DNA" *Nature* (1993) 361:365–369.

Monaghan et al., "Ultrastructural localization of BCL–2 protein" *J. Histochem. Cytochem.* (1992) 40:1819–1825.

Lehrach et al., "RNA molecular weight determinations by gel electrophoresis under denaturing conditions, a critical reexamination" *Biochem.* (1977) 16:4743–4751.

Thomas, "Hybridization of denatured RNA and small DNA fragments transferred to nitrocellulose" *Proc. Natl. Acad. Sci. USA* (1980) 77:5201–5205.

Barr, "Expression of Foreign genes in yeast" *Transgenesis* (1992) Murray, J.A.H., ed., Wiley & Sons, New York, p. 55–79.

Henderson et al., "Epstein–Barr virus–coded BHRF1 protein, a viral homologue of Bci–2, protects human B cells from programmed cell death" *Proc. Natl. Acad. Sci. USA* (1993) 90:8479–8483.

Viegas–Péquignot, "In situ hybridization to chromosomes with biotinylated probes" *In Situ Hybridization. A Practical Approach,* D.G. Wilkinson, ed., IRL Press, Oxford, pp. 137–158.

Pinkel et al., "Fluorescence in situ hybrization with human chromosome–specific libraries: Detection of trisomy 21 and translocations of chromosome 4" *Proc. Natl. Acad. Sci. USA* (1988) 85:9138–9142.

McKearn et al., "Enrichment of hematopoietic precursor cells and cloning of multipotential B–lymphocyte precursrs" *Proc. Natl. Acad. Sci. USA* (1985) 82:7414–7418.

Nuñez et al., "Deregulated Bcl–2 gene expression selectively prolongs survival of growth factor–deprived hemopoietic cell lines" *J. Immunol.* (1990) 144:3602–3610.

Hockenbery et al., "Bcl–2 is an inner mitochondrial protein that blocks programmed cell death" *Nature* (190) 348:334–336.

Cherif et al., "Ordering markers in the region of the ataxia–telangiectasia gene (11q22–q23) by fluorescence in situ hybridization (FISH) to interphase nuclei" *Hum. Genet.* (1994) 93:1–6.

Foroud et al., "Localization of an ataxia–telangiectasia locus to a 3–cM interval on chromosome 11q23: Linkage analysis of III families by an international consortium" *Am. J. Hum. Genet.* (1991) 49:1263–1279.

Kapp et al., "Cloning of a candidate gene for ataxia–telangiectasia group D" *Am. J. Hum. Genet.* (1992) 51:45–54.

Khati et al., "Genetic heterogeneity of autosomal dominant cerebellar ataxia type 1: Clinical and genetic analysis of 10 French families" *Neurology* (1993) 43:1131–1137.

Meyn, "Ataxia–telangiectasia, apoptosis and cellular responses to DNA damage: A Model" *Cancer Genet.* (1993) 53:(Abstract no. 1529).

Orr et al., "Expansion of an unstable trinucleotide CAG repeat in spinocerebellar ataxia type 1" *Nature Genetics* (1993) 4:221–226.

Kennedy, "Prevention of carcinogenesis by protease inhibitors" *Cancer Res.* (1994) 54:1999s–2005s.

Lam et al., "Evidence that BCL–2 represses apoptosis by regulating endoplasmic reticulum–associated $Ca^{2+}$ fluxes" *Proc. Natl. Acad. Sci. USA* (1994) 91:6569–6573.

Reed et al., "Antisense–mediated inhibition of BCL2 protooncogene expression and leukemic cell growth and survival: Comparisons of phosphodiester and phosphorothioate oligodeoxynucleotides" *Cancer Res.* (1990) 50:6565–6570.

Yonehara et al., "A cell–killing monoclonal antibody (ANTI–Fas) to a cell surface antigen co–downregulated with the receptor of tumor necrosis factor" *J. Exp. Med.* (1989) 169:1747–1756.

Sato et al., "Interactions among members of the Bcl–2 protein family analyzed with a yeast two–hybrid system" *Proc. Natl. Acad. Sci. USA* (1994) 91:9238–9242.

Pearson et al., "Identification of an Epstein–Barr virus early gene encoding a second component of the restricted early antigen complex" *Virol.* (1987) 160:151–161.

Reeck et al., 1987, Cell 50:667.

Lewin, 1987, Science 237:1570.

Fig. 1A

```
GAGGATCTAC AGGGACAAG TAAAGGCTAC ATCCAGATGC CGGGAATGCA CTGACGCCCA         60
TTCCTGGAAA CTGGGCTCCC ACTCAGCCCC TGGGAGCAGC AGCCGCCAGC CCCTCGGACC        120
TCCATCTCCA CCCTGCTGAG CCACCCCGGT TGGGCCAGGA TCCCGGCAGG CTGATCCCGT        180
CCTCCACTGA GACCTGAAAA ATG GCT TCG GGG CAA GGC CCA GGT CCT CCC           230
                        Met Ala Ser Gly Gln Gly Pro Gly Pro Pro
                         1               5                  10

AGG CAG GAG TGC GGA GAG CCT GCC CTG CCC TCT GCT TCT GAG GAG CAG         278
Arg Gln Glu Cys Gly Glu Pro Ala Leu Pro Ser Ala Ser Glu Glu Gln
                15                  20                  25

GTA GCC CAG GAC ACA GAG GAG GTT TTC CGC TAC AGC GTT GCT GCC GAC CCA     326
Val Ala Gln Asp Thr Glu Glu Val Phe Arg Tyr Ser Val Ala Ala Asp Pro
            30                  35                  40

CAT CAG GAA CAG GAG GCT GCT GAA CAG GGT GTG GCT GCC CCT GCC GAC CCA     374
His Gln Glu Gln Glu Ala Ala Glu Gln Gly Val Ala Ala Pro Ala Asp Pro
        45                  50                  55

GAG ATG GTC ACC TTA CCT CTG CAA CCT AGC AGC ACC ATG GGG CAG GTG         422
Glu Met Val Thr Leu Pro Leu Gln Pro Ser Ser Thr Met Gly Gln Val
    60                  65                  70

GGA CGG GCC CAG CTC ATC ATC GGG GAC GAC ATC AAC AGA CGA TAT GAC         470
Gly Arg Ala Gln Leu Ile Ile Gly Asp Asp Ile Asn Arg Arg Tyr Asp
75                  80                  85                  90

TCA GAG TTC CAG ACC ATG TTG CAG CAC CTG CAG CCC ACG GCA GAG AAT         518
Ser Glu Phe Gln Thr Met Leu Gln His Leu Gln Pro Thr Ala Glu Asn
                95                  100                 105
```

Fig. 1B

```
GCC TAT GAG TAC TTC ACC AAG ATT GCC ACC AGC CTG TTT GAG AGT GGC      566
Ala Tyr Glu Tyr Phe Thr Lys Ile Ala Thr Ser Leu Phe Glu Ser Gly
        110                 115                 120

ATC AAT TGG GGC CGT GTG GCT GTG CTT CTG GGC TTC GGC TAC CGT CTG      614
Ile Asn Trp Gly Arg Val Ala Val Leu Leu Gly Phe Gly Tyr Arg Leu
        125                 130                 135

GCC CTA CAC GTC TAC CAG CAT GGC CTG ACT GGC TTC CTA GGC CAG GTG      662
Ala Leu His Val Tyr Gln His Gly Leu Thr Gly Phe Leu Gly Gln Val
        140                 145                 150

ACC CGC TTC GTG GTC GAC ATG TTC CTG ACT CAT CAC TGC ATT GGT TGG      710
Thr Arg Phe Val Val Asp Met Phe Leu Thr His His Cys Ile Gly Trp
        155                 160                 165                 170

ATT GCA CAG AGG GGT GGC TGG GTG GCA GCC CTG AAC TTG GGC AAT GGT      758
Ile Ala Gln Arg Gly Gly Trp Val Ala Ala Leu Asn Leu Gly Asn Gly
        175                 180                 185

CCC ATC CTG AAC GTG CTG GTG GTT CTG TTG GGC CAG      806
Pro Ile Leu Asn Val Leu Val Val Leu Leu Gly Gln
        190                 195                 200

TTT GTG GTA CGA AGA TTC TTC AAA TCA TGACTCCCAA GGGTGCCCTT      853
Phe Val Val Arg Arg Phe Phe Lys Ser
        205                 210

TGGGTCCCGG TTCAGACCCC TGCCTGGACT TAAGCGAAGT CTTTGCCTTC TCTGTTCCCT      913

TGCAGGGTCC CCCCTCAAGA GTACAGAAGC TTTAGCAAGT GTGCACTCCA GCTTCGGAGG      973

CCCTGCGTGG GGGCCAGTCA GGCTGCAGAG GCACCTCAAC ATTGCATGGT GCTAGTGCCC      1033

TCTCTCTGGG CCCAGGGCTG TGGCCGTCTC CTCCCTCAGC TCTCTGGGAC CTCCTTAGCC      1093
```

Fig. 1C

| | | | | | |
|---|---|---|---|---|---|
| CTGTCTGCTA | GGGCGCTGGGG | AGACTGATAA | CTTGGGGAGG | CAAGAGACTG | GGAGCCACTT | 1153 |
| CTCCCCAGAA | AGTGTTTAAC | GGTTTTAGCT | TTTTATAATA | CCCTTGTGAG | AGCCCATTCC | 1213 |
| CACCATTCTA | CCTGAGGCCA | GGACGTCTGG | GGTGTGGGGA | TTGGTGGGTC | TATGTTCCCC | 1273 |
| AGGATTCAGC | TATTCTGGAA | GATCAGCACC | CTAAGAGATG | GGACTAGGAC | CTGAGCCTGG | 1333 |
| TCCTGGCCGT | CCCTAAGCAT | GTGTCCCAGG | AGCAGGACCT | ACTAGGAGAG | GGGGGCCAAG | 1393 |
| GTCCTGCTCA | ACTCTACCCC | TGCTCCCATT | CCTCCCCTCCG | GCCATACTGC | CTTTGCAGTT | 1453 |
| GGACTCTCAG | GGATTCTGGG | CTTGGGGTGT | GGGGTGGGGT | GGAGTCGCAG | ACCAGAGCTG | 1513 |
| TCTGAACTCA | CGTGTCAGAA | GCCTCCAAGC | ACTTGCTCCC | CTGCCTCCCA | AGTCCTCTC | 1573 |
| CTTCCCTCT | CCTTATAGAC | ACTTGCTCCC | AACCCATTCA | CTACAGGTGA | AGGCTCTCAC | 1633 |
| CCATCCCTGG | GGGCCTTGGG | TGAGTGGCCT | GCTAAGGCTC | CTCCCTTGCCC | AGACTACAGG | 1693 |
| GCTTAGGACT | TGGTTTGTTA | TATCAGGGAA | AAGGAGTAGG | GAGTTCATCT | GGAGGGTTCT | 1753 |
| AAGTGGGAGA | AGGACTATCA | ACACCACTAG | GAATCCCAGA | GGTGGATCCT | CCCTCATGGC | 1813 |
| TCTGGCACAG | TGTAATCCAG | GGGTGTAGAT | GGGGGAACTG | TGAATACTTG | AACTCTGTTC | 1873 |
| CCCCACCCTC | CATGCTCCTC | ACCTGTCTAG | GTCTCCTCAG | GGTGGGGGGT | GACAGTGCCT | 1933 |
| TCTCTATTGG | CACAGCCTAG | GGTCTTGGGG | GTCAGGGGGG | AGAAGTTCTT | GATTCAGCCA | 1993 |
| AATGCAGGGA | GGGGAGGCAG | ATGGAGCCCA | TAGGCCACCC | CCTATCCCTCT | GAGTGTTTGG | 2053 |
| AAATAAACTG | TGCAATCCCC | TCAAAAAAAA | AACGGAGATC | C | | 2094 |

Fig. 2A

```
         10          20          30          40          50          60
         *           *           *           *           *           *
TTT TAA TAT AAA TTA ATG TGC TCT ATT TAT AGA GAC AAT ACA TGA AAT ATA CTT AAT AAA
AAA ATT ATA TTT AAT TAC ACG AGA TAA TAA ATA TCT CTG TTA TGT ACT TTA TAT GAA TTA TTT 70          80          90          100         110         120
         *           *           *           *           *           *
AAT TCA AAT GTT ATA GAA CTG TTT AAA AAG ATG AAA AGT AAC CTA TTC CCC AGA GGT
TTA AGT TTA CAA TAT CTT GAC AAA TTT TTC TAC TTT TCA TTG TTG GAT AAG GGG TCT CCA 130         140         150         160         170         180
         *           *           *           *           *           *
AGC CAC TGT CCA TAG TTT CTA TTT TAG TCC TTT ATA CAA GAT TAT TAT AGC TTC
TCG GTG ACA GGT ATC AAA GAT AAA ATC AGG AAA TAT GTT CTA ATA TCG AAG 190         200         210         220         230         240
         *           *           *           *           *           *
TAT TTT TTG GTG TAT GAA CTT AGT TGC TAA GAA ATT CGT AGA TTA GTT CAT ATG AGT TCT ATA ACT
ATA TAA AAC CAC ATA CTT GAA TCA ACG ATT CTT TAA GCA TCT CAA AAT TAC ATG CAA TAT TGA TAT AGA TGA 250         260         270         280         290         300
         *           *           *           *           *           *
AAG ATC CAT CAT CTT AGT TGC TAA TGA GAA TAC ATG CAT CAT TTA AAA AAA CAT
TTC TAG GTA GTA GAA TCA ACG ATT ACT CTT ATG TAC GTA GTA AAT TTT TTT GTA 310         320         330         340         350         360
         *           *           *           *           *           *
TTT TGG CTG GCA CCT CAT GAT CAC TGG AGT CTC GCG GGT CCC TCA GGC TGC ACA GGG ACA
AAA ACC GAC CGT GGA GTC CTA GTG ACC TCA GAG CGC CCA GGG AGT CCG ACG TGT CCC TGT 370         380         390         400         410         420
         *           *           *           *           *           *
AGT AAA GGC TAC ATC CAG ATG CTG GGA ATG CAC TGA CCA TTC CTG GAA ACT GGG CTC
TCA TTT CCG ATG TAG GTC TAC GAC CCT TAC GTG ACT GGT AAG GAC CTT TGA CCC GAG
```

```
            790                 800                 810                 820                 830                 840
             *                   *                   *                   *                   *                   *
ATC ATT GGG GAC GAC ATC AAC CGA CGC TAT GAC TCA GAG TTC CAG ACC ATG TTG CAG CAC
TAG TAA CCC CTG CTG TAG TTG GCT GCG ATA CTG AGT CTC AAG TGG TAC AAC GTC GTG
 I   I   G   D   D   I   N   R   R   Y   D   S   E   F   Q   T   M   L   Q   H

Pst1   850                 860                 870                 880                 890                 900
             *                   *                   *                   *                   *                   *
CTG CAG CCC ACG GCA GAG AAT GCC TAT ATA CGG AAG ATT ACC TTC AAG GCC TCC AGC TTT
GAC GTC GGG TGC CGT CTC TTA CGG ATA TAT GCC TTC TAA TGG AAG TTC CGG AGG TCG AAA
 L   Q   P   T   A   E   N   A   Y   I   R   K   I   T   F   K   A   S   S   F 910                 920                 930                 940                 950                 960
             *                   *                   *                   *                   *                   *
GAG AGT GGC ATC AAT TGG ACC GTG CAC CTG GCT CTT GGC TTC TAC AGC CGT CTG GCC
CTC TCA CCG TAG TTA ACC TGG CAC GTG GAC CGA GAA CCG AAG ATG TCG GCA GAC CGG
 E   S   G   I   N   W   T   V   H   L   A   L   G   F   S   Y   R   L   A 970                 980                 990                 1000                1010                1020
             *                   *                   *                   *                   *                   *
CTA CAC ATC TAC CAG CGT GGC CTG ACT GGC CTG GTG CAG ACC CGC TTT AAA CTG GTG
GAT GTG TAG ATG GTC GCA CCG GAC TGA CCG GAC CAC GTC TGG GCG AAA TTT GAC CAC
 L   H   I   Y   Q   R   G   L   T   G   L   V   Q   T   R   F   K   L   V 1030                1040                1050                1060                1070                1080
             *                   *                   *                   *                   *                   *
GAC TTC ATG CTG CAT CAC TGC ATT GCC CGG TGG GCA CAG AGG GGT TGG GTG GTG GCA
CTG AAG TAC GAC GTA GTG ACG TAA CGG GCC ACC GTC TCC CCA ACC CAC CAC CGT
 D   F   M   L   H   H   C   I   A   R   W   A   Q   R   G   W   V   V   A
```

Fig. 2D

```
         1090      1100      1110      1120      1130      1140
          *         *         *         *         *         *
GCC CTG AAC TTG GGC AAT GGT CCC ATC CTG AAC GTG CTG GAC GTG GTT CTG GGT GTG CAC GTG GTT CTG GAC
CGG GAC TTG AAC CCG TTA CCA GGG TAG GAC TTG CAC GAC CTG CAA CCA CAC GTT GAC CAA GAC
 A   L   N   L   G   N   G   P   I   L   N   V   L   D   V   G   V   H   V   V   L   D 1150      1160      1170      1180      1190      1200
          *         *         *         *         *         *
TTG GGC CAG TTT GTG GTA CAT CGA AGA TTC AAG TCA TGA CTC CCA AGG GTG CCT TTG GGG
AAC CCG GTC AAA CAC GTA GCT TCT AAG TTC AGT ACT GAG GGT TCC CAC GGA AAC CCC
 L   G   Q   F   V   V   H   R   R   F   K   F   K   S   *

1210      1220      1230      1240      1250      1260
          *         *         *         *         *         *
TCC CAG TTC AGA CCC CTG CCT GGA CTT AAG CGA AGT CTT TGC TCC TTG CAG
AGG GTC AAG TCT GGG GAC GGA CCT GAA TTC GCT TCA GAA ACG AGG AAC GTC 1270      1280   Hind3
          *         *       |
GGT CCC CCC TCA AGA GTA CAG AAG CTT
CCA GGG GGG AGT TCT CAT GTC TTC GAA
```

1) *In vitro* co-translated proteins
2) Proteins bound to anti-FLAG agarose

SEQUENCE LISTING (1) GENERAL INFORMATION:

(iii) NUMBER OF SEQUENCES: 4

(2) INFORMATION FOR SEQ ID NO:1:

(i) SEQUENCE CHARACTERISTICS:
      (A) LENGTH: 2094 base pairs
      (B) TYPE: nucleic acid
      (C) STRANDEDNESS: single
      (D) TOPOLOGY: linear (ix) FEATURE:
      (A) NAME/KEY: CDS
      (B) LOCATION: 201..833

(xi) SEQUENCE DESCRIPTION: SEQ ID NO:1:

```
GAGGATCTAC AGGGGACAAG TAAAGGCTAC ATCCAGATGC CGGGAATGCA CTGACGCCCA        60

TTCCTGGAAA CTGGGCTCCC ACTCAGCCCC TGGGAGCAGC AGCCGCCAGC CCCTCGGACC       120

TCCATCTCCA CCCTGCTGAG CCACCCGGGT TGGGCCAGGA TCCCGGCAGG CTGATCCCGT       180

CCTCCACTGA GACCTGAAAA ATG GCT TCG GGG CAA GGC CCA GGT CCT CCC          230
                       Met Ala Ser Gly Gln Gly Pro Gly Pro Pro
                        1               5                  10
```

```
AGG CAG GAG TGC GGA GAG CCT GCC CTG CCC TCT GCT TCT GAG GAG CAG         278
Arg Gln Glu Cys Gly Glu Pro Ala Leu Pro Ser Ala Ser Glu Glu Gln
             15                  20                  25

GTA GCC CAG GAC ACA GAG GAG GTT TTC CGC AGC TAC GTT TTT TAC CGC         326
Val Ala Gln Asp Thr Glu Glu Val Phe Arg Ser Tyr Val Phe Tyr Arg
             30                  35                  40

CAT CAG CAG GAA CAG GAG GCT GAA GGG GTG GCT GCC CCT GCC GAC CCA         374
His Gln Gln Glu Gln Glu Ala Glu Gly Val Ala Ala Pro Ala Asp Pro
             45                  50                  55

GAG ATG GTC ACC TTA CCT CTG CAA CCT AGC AGC ACC ATG GGG CAG GTG         422
Glu Met Val Thr Leu Pro Leu Gln Pro Ser Ser Thr Met Gly Gln Val
             60                  65                  70

GGA CGG CAG CTC GCC ATC ATC GGG GAC GAC ATC AAC CGA CGC TAT GAC         470
Gly Arg Gln Leu Ala Ile Ile Gly Asp Asp Ile Asn Arg Arg Tyr Asp
75                  80                  85                  90

TCA GAG TTC CAG ACC ATG TTG CAG CAC CTG CAG CCC ACG GCA GAG AAT         518
Ser Glu Phe Gln Thr Met Leu Gln His Leu Gln Pro Thr Ala Glu Asn
                 95                 100                 105

GCC TAT GAG TAC TTC ACC AAG ATT GCC ACC AGC CTG TTT GAG AGT GGC         566
Ala Tyr Glu Tyr Phe Thr Lys Ile Ala Thr Ser Leu Phe Glu Ser Gly
            110                 115                 120

ATC AAT TGG GGC CGT GTG GTG GCT CTT CTG GGC TTC GGC TAC CGT CTG         614
Ile Asn Trp Gly Arg Val Val Ala Leu Leu Gly Phe Gly Tyr Arg Leu
            125                 130                 135

GCC CTA CAC GTC TAC CAG CAT GGC CTG ACT GGC TTC CTA GGC CAG GTG         662
Ala Leu His Val Tyr Gln His Gly Leu Thr Gly Phe Leu Gly Gln Val
        140                 145                 150

ACC CGC TTC GTG GTC GAC TTC ATG CTG CAT CAC TGC ATT GCC CGG TGG         710
Thr Arg Phe Val Val Asp Phe Met Leu His His Cys Ile Ala Arg Trp
155                 160                 165                 170

ATT GCA CAG AGG GGT GGC TGG GTG GCA GCC CTG AAC TTG GGC AAT GGT         758
Ile Ala Gln Arg Gly Gly Trp Val Ala Ala Leu Asn Leu Gly Asn Gly
            175                 180                 185

CCC ATC CTG AAC GTG CTG GTG GTT CTG GGT GTG GTT CTG TTG GGC CAG         806
Pro Ile Leu Asn Val Leu Val Val Leu Gly Val Val Leu Leu Gly Gln
            190                 195                 200

TTT GTG GTA CGA AGA TTC TTC AAA TCA TGACTCCCAA GGGTGCCCTT              853
Phe Val Val Arg Arg Phe Phe Lys Ser
            205                 210

TGGGTCCCGG TTCAGACCCC TGCCTGGACT TAAGCGAAGT CTTTGCCTTC TCTGTTCCCT       913

TGCAGGGTCC CCCCTCAAGA GTACAGAAGC TTTAGCAAGT GTGCACTCCA GCTTCGGAGG       973

CCCTGCGTGG GGGCCAGTCA GGCTGCAGAG GCACCTCAAC ATTGCATGGT GCTAGTGCCC      1033

TCTCTCTGGG CCCAGGGCTG TGGCCGTCTC CTCCCTCAGC TCTCTGGGAC CTCCTTAGCC      1093

CTGTCTGCTA GGCGCTGGGG AGACTGATAA CTTGGGGAGG CAAGAGACTG GGAGCCACTT      1153

CTCCCCAGAA AGTGTTTAAC GGTTTTAGCT TTTTATAATA CCCTTGTGAG AGCCCATTCC      1213

CACCATTCTA CCTGAGGCCA GGACGTCTGG GGTGTGGGGA TTGGTGGGTC TATGTTCCCC      1273

AGGATTCAGC TATTCTGGAA GATCAGCACC CTAAGAGATG GGACTAGGAC CTGAGCCTGG      1333

TCCTGGCCGT CCCTAAGCAT GTGTCCCAGG AGCAGGACCT ACTAGGAGAG GGGGGCCAAG      1393

GTCCTGCTCA ACTCTACCCC TGCTCCCATT CCTCCCTCCG GCCATACTGC CTTTGCAGTT      1453

GGACTCTCAG GGATTCTGGG CTTGGGGTGT GGGGTGGGGT GGAGTCGCAG ACCAGAGCTG      1513

TCTGAACTCA CGTGTCAGAA GCCTCCAAGC CTGCCTCCCA AGGTCCTCTC AGTTCTCTCC      1573

CTTCCTCTCT CCTTATAGAC ACTTGCTCCC AACCCATTCA CTACAGGTGA AGGCTCTCAC      1633

CCATCCCTGG GGGCCTTGGG TGAGTGGCCT GCTAAGGCTC CTCCTTGCCC AGACTACAGG      1693
```

```
GCTTAGGACT TGGTTTGTTA TATCAGGGAA AAGGAGTAGG GAGTTCATCT GGAGGGTTCT      1753

AAGTGGGAGA AGGACTATCA ACACCACTAG GAATCCCAGA GGTGGATCCT CCCTCATGGC      1813

TCTGGCACAG TGTAATCCAG GGGTGTAGAT GGGGGAACTG TGAATACTTG AACTCTGTTC      1873

CCCCACCCTC CATGCTCCTC ACCTGTCTAG GTCTCCTCAG GGTGGGGGT GACAGTGCCT       1933

TCTCTATTGG CACAGCCTAG GGTCTTGGGG GTCAGGGGGG AGAAGTTCTT GATTCAGCCA      1993

AATGCAGGGA GGGGAGGCAG ATGGAGCCCA TAGGCCACCC CCTATCCTCT GAGTGTTTGG      2053

AAATAAACTG TGCAATCCCC TCAAAAAAAA AACGGAGATC C                          2094
```

(2) INFORMATION FOR SEQ ID NO:2:

(i) SEQUENCE CHARACTERISTICS:
        (A) LENGTH: 211 amino acids
        (B) TYPE: amino acid
        (D) TOPOLOGY: linear (ii) MOLECULE TYPE: protein (xi) SEQUENCE DESCRIPTION: SEQ ID NO:2:

```
Met Ala Ser Gly Gln Gly Pro Gly Pro Pro Arg Gln Glu Cys Gly Glu
 1               5                  10                  15

Pro Ala Leu Pro Ser Ala Ser Glu Glu Gln Val Ala Gln Asp Thr Glu
            20                  25                  30

Glu Val Phe Arg Ser Tyr Val Phe Tyr Arg His Gln Gln Glu Gln Glu
        35                  40                  45

Ala Glu Gly Val Ala Ala Pro Ala Asp Pro Glu Met Val Thr Leu Pro
    50                  55                  60

Leu Gln Pro Ser Ser Thr Met Gly Gln Val Gly Arg Gln Leu Ala Ile
65                  70                  75                  80

Ile Gly Asp Asp Ile Asn Arg Arg Tyr Asp Ser Glu Phe Gln Thr Met
                85                  90                  95

Leu Gln His Leu Gln Pro Thr Ala Glu Asn Ala Tyr Glu Tyr Phe Thr
            100                 105                 110

Lys Ile Ala Thr Ser Leu Phe Glu Ser Gly Ile Asn Trp Gly Arg Val
        115                 120                 125

Val Ala Leu Leu Gly Phe Gly Tyr Arg Leu Ala Leu His Val Tyr Gln
    130                 135                 140

His Gly Leu Thr Gly Phe Leu Gly Gln Val Thr Arg Phe Val Val Asp
145                 150                 155                 160

Phe Met Leu His His Cys Ile Ala Arg Trp Ile Ala Gln Arg Gly Gly
                165                 170                 175

Trp Val Ala Ala Leu Asn Leu Gly Asn Gly Pro Ile Leu Asn Val Leu
            180                 185                 190

Val Val Leu Gly Val Val Leu Leu Gly Gln Phe Val Val Arg Arg Phe
        195                 200                 205

Phe Lys Ser
    210
```

(2) INFORMATION FOR SEQ ID NO:3:

(i) SEQUENCE CHARACTERISTICS:
        (A) LENGTH: 1287 base pairs
        (B) TYPE: nucleic acid
        (C) STRANDEDNESS: single
        (D) TOPOLOGY: linear (ix) FEATURE:
        (A) NAME/KEY: CDS
        (B) LOCATION: 544..1176

```
    (xi) SEQUENCE DESCRIPTION: SEQ ID NO:3:

TTTTAATATA AATTAATGTG CTCTATTTAT AGAGACAATA CATGAAATAT ACTTAATAAA     60

AATTCAAATG TTATAGAACT GAAAAAGATG AAAAGTAAAA ACAACCTATT CCCCAGAGGT    120

AGCCACTGTC CATAGTTTCT ATTTTAGATT CTTTCCTTTA TACAAGATTA TTATAGCTTC    180

TATTTTTTGG TGTATGAACT GTAGTCCTAG AGGATTTTAT TAGTTATGAG TTCTATAACT    240

AAGATCCATC ATCTTAGTTG CTAAGAACGT AGATACTGAG AACATCATTT AAAAAAACAT    300

TTTTGGCTGG CACCTCATGA TCACTGGAGT CTCGCGGGTC CCTCAGGCTG CACAGGGACA    360

AGTAAAGGCT ACATCCAGAT GCTGGGAATG CACTGACGCC CATTCCTGGA AACTGGGCTC    420

CCACTCAGCC CCTGGGAGCA GCAGCCGCCA GCCCCTCGGG ACCTCCATCT CCACCCTGCT    480

GAGCCACCCG GGTTGGGCCA GGATCCCGGC AGGCTGATCC CGTCCTCCAC TGAGACCTGA    540

AAA ATG GCT TCG GGG CAA GGC CCA GGT CCT CCC AGG CAG GAG TGC GGA      588
    Met Ala Ser Gly Gln Gly Pro Gly Pro Pro Arg Gln Glu Cys Gly
                215                 220                 225

GAG CCT GCC CTG CCC TCT GCT TCT GAG GAG CAG GTA GCC CAG GAC ACA      636
Glu Pro Ala Leu Pro Ser Ala Ser Glu Glu Gln Val Ala Gln Asp Thr
            230                 235                 240

GAG GAG GTT TTC CGC AGC TAC GTT TTT TAC CAC CAT CAG CAG GAA CAG      684
Glu Glu Val Phe Arg Ser Tyr Val Phe Tyr His His Gln Gln Glu Gln
        245                 250                 255

GAG GCT GAA GGG GCG GCT GCC CCT GCC GAC CCA GAG ATG GTC ACC TTA      732
Glu Ala Glu Gly Ala Ala Ala Pro Ala Asp Pro Glu Met Val Thr Leu
    260                 265                 270

CCT CTG CAA CCT AGC AGC ACC ATG GGG CAG GTG GGA CGG CAG CTC GCC      780
Pro Leu Gln Pro Ser Ser Thr Met Gly Gln Val Gly Arg Gln Leu Ala
275                 280                 285                 290

ATC ATT GGG GAC GAC ATC AAC CGA CGC TAT GAC TCA GAG TTC CAG ACC      828
Ile Ile Gly Asp Asp Ile Asn Arg Arg Tyr Asp Ser Glu Phe Gln Thr
                295                 300                 305

ATG TTG CAG CAC CTG CAG CCC ACG GCA GAG AAT GCC TAT GAG TAC TTC      876
Met Leu Gln His Leu Gln Pro Thr Ala Glu Asn Ala Tyr Glu Tyr Phe
            310                 315                 320

ACC AAG ATT GCC TCC AGC CTG TTT GAG AGT GGC ATC AAT TGG GGC CGT      924
Thr Lys Ile Ala Ser Ser Leu Phe Glu Ser Gly Ile Asn Trp Gly Arg
        325                 330                 335

GTG GTG GCT CTT CTG GGC TTC AGC TAC CGT CTG GCC CTA CAC ATC TAC      972
Val Val Ala Leu Leu Gly Phe Ser Tyr Arg Leu Ala Leu His Ile Tyr
    340                 345                 350

CAG CGT GGC CTG ACT GGC TTC CTG GGC CAG GTG ACC CGC TTT GTG GTG     1020
Gln Arg Gly Leu Thr Gly Phe Leu Gly Gln Val Thr Arg Phe Val Val
355                 360                 365                 370

GAC TTC ATG CTG CAT CAC TGC ATT GCC CGG TGG ATT GCA CAG AGG GGT     1068
Asp Phe Met Leu His His Cys Ile Ala Arg Trp Ile Ala Gln Arg Gly
                375                 380                 385

GGC TGG GTG GCA GCC CTG AAC TTG GGC AAT GGT CCC ATC CTG AAC GTG     1116
Gly Trp Val Ala Ala Leu Asn Leu Gly Asn Gly Pro Ile Leu Asn Val
            390                 395                 400

CTG GTG GTT CTG GGT GTG GTT CTG TTG GGC CAG TTT GTG GTA CGA AGA     1164
Leu Val Val Leu Gly Val Val Leu Leu Gly Gln Phe Val Val Arg Arg
        405                 410                 415

TTC TTC AAA TCA TGACTCCCAA GGGTGCCTTT GGGGTCCCAG TTCAGACCCC         1216
Phe Phe Lys Ser
    420

TGCCTGGACT TAAGCGAAGT CTTTGCCTTC TCTGCTCCTT GCAGGGTCCC CCCTCAAGAG   1276

TACAGAAGCT T                                                        1287
```

(2) INFORMATION FOR SEQ ID NO:4:

(i) SEQUENCE CHARACTERISTICS:
        (A) LENGTH: 211 amino acids
        (B) TYPE: amino acid
        (D) TOPOLOGY: linear (ii) MOLECULE TYPE: protein (xi) SEQUENCE DESCRIPTION: SEQ ID NO:4:

```
Met Ala Ser Gly Gln Gly Pro Gly Pro Pro Arg Gln Glu Cys Gly Glu
 1               5                  10                  15

Pro Ala Leu Pro Ser Ala Ser Glu Glu Gln Val Ala Gln Asp Thr Glu
             20                  25                  30

Glu Val Phe Arg Ser Tyr Val Phe Tyr His His Gln Gln Glu Gln Glu
             35                  40                  45

Ala Glu Gly Ala Ala Ala Pro Ala Asp Pro Glu Met Val Thr Leu Pro
 50                  55                  60

Leu Gln Pro Ser Ser Thr Met Gly Gln Val Gly Arg Gln Leu Ala Ile
 65                  70                  75                  80

Ile Gly Asp Asp Ile Asn Arg Arg Tyr Asp Ser Glu Phe Gln Thr Met
                 85                  90                  95

Leu Gln His Leu Gln Pro Thr Ala Glu Asn Ala Tyr Glu Tyr Phe Thr
                100                 105                 110

Lys Ile Ala Ser Ser Leu Phe Glu Ser Gly Ile Asn Trp Gly Arg Val
            115                 120                 125

Val Ala Leu Leu Gly Phe Ser Tyr Arg Leu Ala Leu His Ile Tyr Gln
    130                 135                 140

Arg Gly Leu Thr Gly Phe Leu Gly Gln Val Thr Arg Phe Val Val Asp
145                 150                 155                 160

Phe Met Leu His His Cys Ile Ala Arg Trp Ile Ala Gln Arg Gly Gly
                165                 170                 175

Trp Val Ala Ala Leu Asn Leu Gly Asn Gly Pro Ile Leu Asn Val Leu
            180                 185                 190

Val Val Leu Gly Val Val Leu Leu Gly Gln Phe Val Val Arg Arg Phe
            195                 200                 205

Phe Lys Ser
210
```

SCREENING METHODS FOR THE IDENTIFICATION OF COMPOUNDS CAPABLE OF ABROGATING BAK-BHRF-1 PROTEIN INTERACTIONS

This application is a continuation of United States patent application Ser. No. 08/426,529, filed Apr. 20, 1995, now abandoned, which is a continuation-in-part of U.S. patent application Ser. No. 08/320,157, filed Oct. 07, 1994, which is a continuation-in-part of U.S. patent application Ser. No. 08/160,067, filed Nov. 30, 1993, now abandoned, which was subsequently filed Nov. 30, 1994, as National Stage application PCT/US94/13930.

FIELD OF THE INVENTION

This invention relates to methods of screening for therapeutic agents using novel proteins with apoptosis-modulating activity.

BACKGROUND OF THE INVENTION

Apoptosis is a normal physiologic process that leads to individual cell death. This process of programmed cell death is involved in a variety of normal and pathogenic biological events and can be induced by a number of unrelated stimuli. Changes in the biological regulation of apoptosis also occur during aging and are responsible for many of the conditions and diseases related to aging. Recent studies of apoptosis have implied that a common metabolic pathway leading to cell death may be initiated by a wide variety of signals, including hormones, serum growth factor deprivation, chemotherapeutic agents, ionizing radiation and infection by human immunodeficiency virus (HIV). Wyllie (1980) Nature, 284: 555–556; Kanter et al. (1984) Biochem. Biophys. Res. Commun. 118: 392–399; Duke and Cohen (1986) Lymphokine Res. 5: 289–299; Tomei et al. (1988) Biochem. Biophys. Res. Commun. 155: 324–331; Kruman et al. (1991) J. Cell. Physiol. 148: 267–273; Ameisen and Capron (1991) Immunology Today 12: 102; and Sheppard and Ascher (1992) J. AIDS 5: 143. Agents that modulate the biological control of apoptosis thus have therapeutic utility in a wide variety of conditions.

Apoptotic cell death is characterized by cellular shrinkage, chromatin condensation, cytoplasmic blebbing, increased membrane permeability and interchromosomal DNA cleavage. Kerr et al. (1992) FASEB J. 6: 2450; and Cohen and Duke (1992) Ann. Rev. Immunol. 10: 267. The blebs, small, membrane-encapsulated spheres that pinch off of the surface of apoptotic cells, may continue to produce superoxide radicals which damage surrounding cell tissue and may be involved in inflammatory processes.

Bcl-2 was discovered at the common chromosomal translocation site t(14:18) in follicular lymphomas and results in aberrant over-expression of bcl-2. Tsujimoto et al. (1984) Science 226: 1097–1099; and Cleary et al. (1986) Cell 47: 19–28. The normal function of bcl-2 is the prevention of apoptosis; unregulated expression of bcl-2 in B cells is thought to lead to increased numbers of proliferating B cells which may be a critical factor in the development of lymphoma. McDonnell and Korsmeyer (1991) Nature 349: 254–256; and, for review see, Edgington (1993) Bio/Tech. 11: 787–792. Bcl-2 is also capable of blocking of γ irradiation-induced cell death. Sentman et al. (1991) Cell 67: 879–888; and Strassen (1991) Cell 67: 889–899. It is now known that bcl-2 inhibits most types of apoptotic cell death and is thought to function by regulating an antioxidant pathway at sites of free radical generation. Hockenbery et al. (1993) Cell 75: 241–251.

While apoptosis is a normal cellular event, it can also be induced by pathological conditions and a variety of injuries. Apoptosis is involved in a wide variety of conditions including but not limited to, cardiovascular disease, cancer regression, immunoregulation, viral diseases, anemia, neurological disorders, gastrointestinal disorders, including but not limited to, diarrhea and dysentery, diabetes, hair loss, rejection of organ transplants, prostate hypertrophy, obesity, ocular disorders, stress and aging.

Bcl-2 belongs to a family of proteins some of which have been cloned and sequenced. Williams and Smith (1993) Cell 74: 777–779. It has been shown that various Bcl-2 members have the ability to associate with one another as heterodimers. Itavi et al. (1993) Cell 74: 609–619; and Sato et al. (1994) Proc. Natl. Acad. Sci. USA 91: 9238–9242. Additionally, BHRF1 displays a 25% sequence identity to Bcl-2 (Cleary et al. (1986) Cell 47: 19–28) and has been shown by gene transfer studies to protect B cells from programmed cell death. Henderson et al. (1993) Proc. Natl. Acad. Sci. USA 90: 8479–8483.

The herpesvirus family of viruses typically produce latent and recurrent infections. Herpesvirus genomes are composed of sequences with a short and a long region. Herpesvirus particles have a diameter from 180 nm to 200 nm. Many particles do not contain envelopes. Typically the DNA is wrapped around an associated protein. The herpesvirus has a tendency to persist in a quiescent state for irregular periods of time.

All references cited herein, both supra and infra, are hereby incorporated by reference herein.

SUMMARY OF THE INVENTION

Diagnostic and therapeutic methods utilizing novel bcl-2 homologs, termed Bak and Bak-2, recombinant cells and transgenic animals expressing the Bak and Bak-2 genes and the peptides expressed thereby are provided. Methods of screening for pharmaceutical agents that stimulate, as well as pharmaceutical agents that inhibit Bak and Bak-2 activity levels are also provided. The methods include combining a BAK protein and a viral protein under conditions in which they interact to form a test sample, exposing the test sample to a potential therapeutic agent and monitoring the interaction of the proteins. Potential therapeutic agents which disrupt the interaction compared to control test samples to which no agent has been added are selected for further study.

BRIEF DESCRIPTION OF THE DRAWINGS

FIG. 1 (SEQ ID NO:1 and SEQ ID NO:2) depicts the nucleotide sequence of Bak.

FIG. 2 (SEQ ID NO:3 and SEQ ID NO:4) shows the sequence of the Bak-2 cDNA and flanking sequences and the corresponding predicted amino acid sequence of the Bak-2 protein.

DETAILED DESCRIPTION OF THE INVENTION

Figure 3:
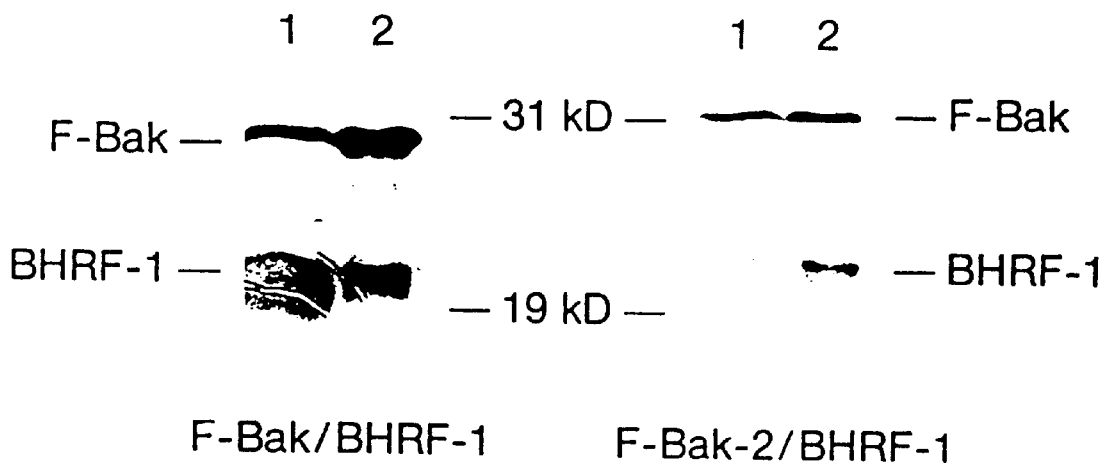
FIG. 3 shows efficient cotranscription and cotranslation of Flag-Bak and BHRF1 and Flag-Bak-2 and BHRF1.

The present invention provides methods of screening for potential anti-viral therapeutic agents. The proteins encoded by nucleotide sequences encoding the novel bcl-2 homologs, Bak and Bak-2 have been found to interact with the Epstein Barr Virus (EBV) protein BHRF1 indicating that BAK proteins contribute to the pathogenicity of the disease. BHRF1 is an EBV early lytic cycle protein. Pearson et al.

(1987) *Virol.* 160: 151–161. The invention thus encompasses methods of exposing the BAK proteins and BHRF1 proteins, or functional portions thereof, to potential therapeutic agents and monitoring the interaction of BAK and BHRF1.

Previous copending applications claim the Bak and Bak-2 nucleotide and protein sequences. Note that in copending United States patent application Serial No. 08/160,067, Bak was termed cdi-1, Bak-2 was termed cdi-2, and in Ser. No. 08/320,157, Bak was termed cdn-1 and Bak-2 was termed cdn-2; although the names have been changed, the nucleotide and amino acid sequences remain identical. The invention further utilizes recombinant cells and transgenic animals expressing the cloned Bak or Bak-2 genes.

Figure 2B:
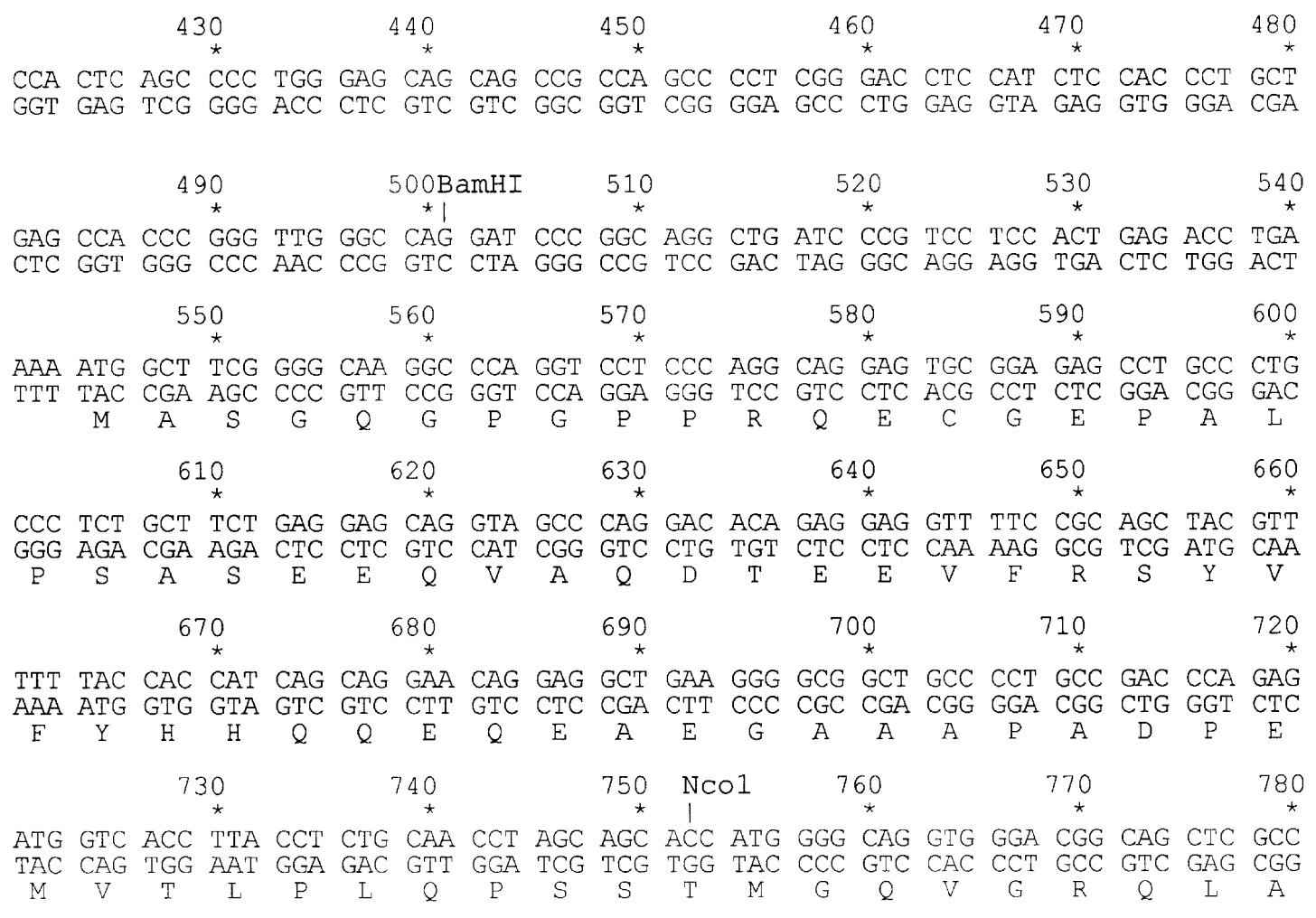

The nucleotide and predicted amino acid residue sequences of Bak are shown in FIG. 1; and those of Bak-2 are shown in FIG. 2. Bak mRNA has been detected in a variety of human organs and tissues by Northern blot analysis. These organs include liver; heart; skeletal muscle; lung; kidney; and pancreas.

It has previously been found that the proteins encoded by the Bak genes are capable of modulating apoptosis. In a lymphoblastoid cell line, Bak was shown to decrease Fas-mediated apoptosis. In a mouse progenitor B cell line, FL5.12, Bak-2 and a derivative of Bak decrease IL-3-induced apoptosis whereas Bak increased apoptosis. Thus, depending on the cell type, the derivative of Bak and the method of induction of apoptosis, apoptosis can be modulated in a highly specific manner by controlling the concentration of BAK proteins.

As used herein, "Baks" or "Bak" refers to the nucleic acid molecules described herein (Bak and Bak-2 derivatives thereof), "the BAKs" or "BAK" refers to the proteins encoded thereby (BAK, BAK-2 and derivatives thereof). The Bak nucleotides include, but are not limited to, the cDNA, genome-derived DNA and synthetic or semi-synthetic DNA or RNA. The nucleotide sequence of the Bak cDNA with the location of restriction endonuclease sites is shown in FIG. 1.

The nucleotide sequence of Bak-2 cDNA, along with the predicted amino acid sequence of Bak-2 protein and the locations of restriction endonuclease recognition sites, is given in FIG. 2. Bak is on human chromosome 6 and Bak-2 is on human chromosome 20. There is also a member of the family, Bak-3, which is on human chromosome 11, however, Bak-3 appears to be a pseudogene. Fluorescence in situ hybridization (FISH) indicated an approximate location of Bak to be at 6p21-23.

The invention includes the use of modified Bak DNA sequences such as deletions, substitutions and additions particularly in the non-coding regions of genomic DNA. Such changes are useful to facilitate cloning and modify gene expression. Any DNA which encodes a portion of a BAK protein sufficient to bind to BHRF1 is suitable for use herein. As described below, various fusion proteins are suitable for use herein.

Various substitutions can be made within the coding region that either do not alter the amino acid residues encoded or result in conservatively substituted amino acid residues. Nucleotide substitutions that do not alter the amino acid residues encoded are useful for optimizing gene expression in different systems. Suitable substitutions are known to those of skill in the art and are made, for instance, to reflect preferred codon usage in the particular expression systems.

The invention encompasses the use of functionally equivalent variants and derivatives of Baks which may enhance, decrease or not significantly affect the properties of BAKs. For instance, changes in the DNA sequence that do not change the encoded amino acid sequence, as well as those that result in conservative substitutions of amino acid residues, one or a few amino acid deletions or additions, and substitution of amino acid residues by amino acid analogs are those which will not significantly affect its properties.

Amino acid residues which can be conservatively substituted for one another include but are not limited to: glycine/alanine; valine/isoleucine/leucine; asparagine/glutamine; aspartic acid/glutamic acid; serine/threonine; lysine/arginine; and phenylalanine/tyrosine. Any conservative amino acid substitution which does not significantly affect the properties of BAKs is encompassed by the present invention.

Techniques for nucleic acid manipulation useful for the practice of the present invention are described in a variety of references, including but not limited to, *Molecular Cloning: A Laboratory Manual,* 2nd ed., Vol. 1–3, eds. Sambrook et al. Cold Spring Harbor Laboratory Press (1989); and *Current Protocols in Molecular Biology*, eds. Ausubel et al., Greene Publishing and Wiley-Interscience: New York (1987) and periodic updates.

As used herein, "BHRF1" or "viral proteins" encompasses the full length EBV protein and portions or derivations thereof sufficient to bind to BAK proteins or portions or derivatives thereof. Such proteins include, but are not limited to, homologous proteins expressed by various forms of herpes and herpes-like viruses, such as cytomegalovirus and varicella zoster.

The interaction between a BAK protein and BHRF-1 can be produced by adding purified proteins together. Preferably, however, the proteins are cotranscribed under conditions which allow protein-protein interactions. Co-transcription can be performed in vitro or in vivo in whole cells expressing native or recombinant BAK and viral proteins. Any suitable recombinant expression vectors may be used.

Methods of monitoring protein interactions are known in the art and any method is suitable for use herein. Preferably, co-precipitation is used. Briefly, the ability of an antibody to precipitate one of the proteins or an immunological tag fused thereto is used to immunoprecipitate the protein and the immunoprecipitate is monitored for the presence of both proteins. Methods of co-precipitation are known in the art and are described in the examples below. Any other method in the art is suitable for use herein, including, but not limited to, protein interactive trapping and ELISA. Immunological tags are often incorporated into fusion proteins and include, but are not limited to, FLAG, hemagglutinin and glutathione-S transferase.

Purification or isolation of BAKs expressed either by the recombinant DNA or from biological sources such as tissues can be accomplished by any method known in the art. Protein purification methods are known in the art. Generally, substantially purified proteins are those which are free of other, contaminating cellular substances, particularly proteins. Preferably, the purified BAKs are more than eighty percent pure and most preferably more than ninety-five percent pure. For clinical use as described below, the BAKs are preferably highly purified, at least about ninety-nine percent pure, and free of pyrogens and other contaminants.

Suitable methods of protein purification are known in the art and include, but are not limited to, affinity chromatography, immunoaffinity chromatography, size exclusion chromatography, HPLC and FPLC. Any purification scheme that does not result in substantial degradation of the protein is suitable for use in the present invention.

Suitable antibodies for use herein are generated by using the BAKs as an antigen or, preferably, peptides encompassing the BAK regions that lack substantial homology to the other gene products of the bcl family. Antibodies to the viral proteins are also suitable for use herein. Methods of detecting proteins using antibodies and of generating antibodies using proteins or synthetic peptides are known in the art and are not described in detail herein.

Screening for therapeutically effective agents is done by exposing the BAKs and the viral protein to such agents which may directly or indirectly affect the interaction between a BAK protein and a viral protein. Suitable potential therapeutic agents include, but are not limited to, any pharmaceutical agent such as cytokines, small molecule drugs, cell-permeable small molecule drugs, hormones, combinations of interleukins, lectins and other stimulating agents, e.g., PMA, LPS, bispecific antibodies, peptide mimetics, antisense oligonucleotides and other agents which modify cellular functions or protein expression.

The proteins are added together or co-expressed, exposed to such agents at physiologically effective concentrations, and the interaction thereof is measured relative to a control not exposed to such agents. Those biological modifiers which decrease the interaction between a BAK protein and a viral protein relative to a control are selected for further study.

As shown in Example 5, overexpressed Bak can protect EBV-transformed B cells from apoptosis following serum withdrawal or anti-Fas treatment. These results indicate that a Bak-BHRF1 interaction exists whereby BHFR1 not only neutralizes the normally apoptotic effect of Bak, but additionally induces a protective activity. Alternatively, propagation of cells transfected with the Bak cDNA might select for cells that are expressing high levels of BHRF1 or other EBV encoded anti-apoptotic proteins. This could lead to an anti-apoptotic response upon subjecting the cells to an apoptosis signal such as serum withdrawal. Example 6 shows that in vitro translated Flag-Bak (epitope tagged) and BHRF1 can be Icoprecipitated with an antibody that recognizes the Flag epitope indicating that Bak and BHRF1 interact directly with one another.

The following examples are provided to illustrate but not limit the present invention. Unless otherwise specified, all cloning techniques were essentially as described by Sambrook et al. (1989) and all reagents were used according to the manufacturer's instructions.

EXAMPLE 1

Identification and Cloning of Bak CDNA

An amino acid sequence comparison of the six known bcl-2 family members revealed two regions with considerable sequence identity, namely amino acids 144–150 and 191–199. In an attempt to identify new bcl-2 family members, degenerate PCR primers based on sequences in these regions were designed and PCR was performed using human heart cDNA and human B lymphoblastoid cell line (WIL-2) cDNA. PCR was performed using the Hot Start/Ampliwax technique (Perkin Elmer Cetus). The final concentration of the PCR primers and the template cDNA were 4 μM and 0.1–0.2 ng/mL, respectively. The conditions for cDNA synthesis were identical to those for first strand cDNA synthesis of the cDNA library as described below. PCR was performed in a Perkin Elmer Cetus DNA Thermal Cycler according to the method described by Kiefer et al. (1991) Biochem. Biophys. Res. Commun. 176: 219–225, except that the annealing and extension temperatures during the first 10 cycles were 36° C. Following PCR, samples were treated with 5 units of DNA polymerase I, Klenow fragment for 30 minutes at 37° C. and then fractionated by electrophoresis on a 7% polyacrylamide, 1×TBE (Tris/borate/EDTA) gel. DNA migrating between 170–210 base pairs was excised from the gel, passively eluted for 16 hours with gentle shaking in 10 mM Tris-HCl pH 7.5, 1 mM EDTA (TE), purified by passage over an Elutip-D column (Schleicher and Schuell), ligated to the pCR-Script vector (Stratagene) and transformed into *Escherichia coli* strain XL1-Blue MRF (Stratagene). Plasmid DNA from transformants (white colonies) containing both the heart and WIL-2 PCR products was isolated using the Magic Miniprep DNA Purification System (Promega), and the DNA inserts were sequenced by the dideoxy chain termination method according to Sanger et al. (1977) *Proc. Natl. Acad. Sci. USA* 74: 5463–5467 (USB, Sequenase version 2.0). DNA sequence analysis of the eleven heart PCR products revealed two sequences identical to bcl-x (Boise et al. (1993) *Cell* 74: 597–608) and ten other sequences unrelated to the bcl-2 family.

DNA sequence analyses of the eleven WIL-2 PCR products yielded one bcl-x sequence, five sequences identical to another bcl-2 family member, bax (Oldvai et al. (1993) *Cell* 74: 609–619), four unrelated sequences and one novel bcl-2 related sequence, termed Bak.

To isolate the Bak cDNA, a human heart cDNA library (Clontech) and a WIL-2 cDNA library, constructed as described by Zapf et al. (1990) *J. Biol. Chem.* 265: 14892–14898 were screened using the Bak PCR DNA insert as a probe. The DNA was $^{32}$P-labeled according to the method described by Feinberg and Vogelstein (1984) *Anal. Biochem.* 137: 266–267 and used to screen 150,000 recombinant clones from both libraries according to the method described by Kiefer et al. (1991). Eight positive clones from the WIL-2 cDNA library and two positive clones from the heart cDNA library were identified. Four clones from the WIL-2 cDNA library and two from the heart cDNA library were further purified and plasmid DNA containing the cDNA inserts was excised from the λZAPII vector (Stratagene). The two longest clones, W7 (2.1 kb) and W5 (2.0 kb) were sequenced and shown to contain the Bak probe sequence, thus confirming their authenticity. The heart cDNAs also encoded Bak.

The W7 DNA sequence along with the deduced amino acid residue sequence is shown in FIG. 1. The deduced amino acid sequence of Bak was also aligned for maximum sequence identity with the other bcl-2 family members; there is considerable sequence identity between Bak and other family members between amino acids 100 and 200. Beyond this central region, sequence conservation falls off sharply. Like bcl-2, Bak appears to be an intracellular protein in that it does not contain a either a hydrophobic signal peptide or N-linked glycosylation sites. Bak does contain a hydrophobic C-terminus that is also observed with all bcl-2 family members except LMW5-HL, suggesting its site of anti-apoptotic activity, like that of bcl-2, is localized to a membrane bound organelle such as the mitochondrial membrane, the endoplasmic reticulum or the nuclear membrane. Hockenbery et al. (1990); Chen-Levy et al. (1989) *Mol. Cell. Biol.* 9: 701–710; Jacobsen et al. (1993) *Nature* 361: 365–369; and Monighan et al. (1992) *J. Histochem. Cytochem.* 40: 1819–1825.

EXAMPLE 2

Expression of Recombinant Bak

In order to express recombinant Bak in the baculovirus system, the Bak cDNA generated in Example 1 was used to generate a novel Bak vector, by a PCR methodology as described in Example 1, using primers from the 3' and 5' flanking regions of the gene which contain restriction sites to facilitate cloning. The plasmids were sequenced by the dideoxy terminator method (Sanger et al., 1977) using sequencing kits (USE, Sequenase version 2.0) and internal primers. This was to confirm that no mutations resulted from PCR.

A clone was used to generate recombinant viruses by in vivo homologous recombination between the overlapping sequences of the plasmid and AcNPV wild type baculovirus. After 48 hours post-transfection in insect *Spodoptera frugiperda* clone 9 (SF9) cells, the recombinant viruses were collected, identified by PCR and further purified. Standard procedures for selection, screening and propagation of recombinant baculovirus were performed (Invitrogen). The molecular mass, on sodium dodecyl sulfate-polyacrylamide gel electrophoresis (SDS-PAGE), of the protein produced in the baculovirus system was compared with the predicted molecular mass of Bak according to the amino-acid sequence.

In addition, similar clones can be expressed preferably in a yeast intracellular expression system by any method known in the art, including the method described by Barr et al. (1992) *Transgenesis* ed. JAH Murray, (Wiley and Sons) pp. 55–79.

EXAMPLE 3

Expression of Bak in Mammalian Systems

The Bak coding sequence was excised from a plasmid generated in Example 1, and introduced into plasmids pCEP7, pREP7 and pcDNA3 (Invitrogen) at compatible restriction enzyme sites. pCEP7 was generated by removing the RSV 3'-LTR of pREP7 with XbaI/Asp718, and substituting the CMV promoter from pCEP4 (Invitrogen). 25 μg of each Bak-containing plasmid was electroporated into the B lymphoblastoid cell line WIL-2, and stable hygromycin resistant transformants or G418 resistant transformants (pcDNA3 constructs) expressing Bak were selected.

The coding region of Baks can also be ligated into expression vectors capable of stably integrating into other cell types including but not limited to cardiomyocytes, neural cell lines such as GTI-7 and TNF sensitive cells such as the human colon adenocarcinoma cell line HT29 so as to provide a variety of assay systems to monitor the regulation of apoptosis by Bak.

EXAMPLE 4

Determination of Other Bak Genes and Cloning of the Bak-2 Gene

Southern blot analyses of human genome DNA and a panel of human/rodent somatic cell DNAs indicated that there were at least 3 Bak related genes and that they resided in chromosomes 6, 11 and 20. PCR/sequence analysis of the three hybrid DNAs showed that Bak was on chromosome 6 and that two closely related sequences were on chromosome 20 (designated Bak-2). We have cloned and sequenced the Bak-2 genes. Interestingly, Bak-2 does not contain an intron and does not have all of the features of processed genes that have returned to the genome. Bak-2 has promoter elements upstream of the CCAAT and TATAAA boxes that are probably not transcribed.

The cDNA sequence of Bak-2 is depicted in FIG. 2. 900,000 clones from a human placenta genomic library in the cosmid vector pWE15 (Stratagene, La Jolla, CA) were screened with a 950 bp BglII-HindIII cDNA probe containing the entire coding region of Bak. The probe was $^{32}$P-labeled according to the method of Feinberg and Vogelstein (1984) *Anal. Biochem.* 137: 266–267. The library was processed and screened under high stringency hybridization and washing conditions as described by Sambrook et al. (1989) *Molecular Cloning,* 2nd edition, Cold Spring Harbor Laboratory Press. Ten double positive clones were further purified by replating and screening as above. Plasmid DNA was purified using the Wizard Maxiprep DNA Purification System as described by the supplier (Promega Corp., Madison, Wis.) and analyzed by EcoRI restriction enzyme mapping and Southern blotting. The probe used for Southern blotting and hybridization conditions was the same as above.

The cosmid clones fell into two groups as judged by EcoRI restriction analysis and Southern blotting. Cosmid clones (cos) 1 and 4 and 7 displayed one distinct pattern of EcoRI generated DNA fragments and contained a single 6.5 kb hybridizing EcoRI DNA fragment. Cos2 and Cos9 fell into the second group that was characterized by a 5.5 kb hybridizing EcoRI DNA fragment. The 6.5 kb DNA fragment from cos2 and the 5.5 kb DNA fragment from cos9 were subcloned into pBluescript SK- (Stratagene, La Jolla, Calif.) using standard molecular biological techniques (Sambrook et al. as above). Plasmid DNA was isolated and the DNA inserts from two subclones, A4 (from cos2) and C5 (from cos9) were mapped with BamHI, HindIII and EcoRI and analyzed by Southern blotting as described above. Smaller restriction fragments from both clones were subcloned into M13 sequencing vectors and the DNA sequence was determined.

The sequence of A4 contains an open reading frame that displays 97% amino acid sequence identity with Bak. The high degree of sequence identity of this gene with Bak indicates that it is a new Bak related gene and therefore will be called Bak-2. Bak-2 contains the conserved regions, BH1 and BH2, that are hallmarks of the bcl-2 family, and displays a lower overall sequence identity (~20–30%) to other members, which is also characteristic of the bcl-2 family.

EXAMPLE 5

Modulation of Apoptosis by Bak and Bak-2 in FL5.12 cells

FL5.12 is an IL-3-dependent lymphoid progenitor cell line (McKearn et al. (1985) *Proc. Natl. Acad. Sci USA* 82: 7414–7418) that has been shown to undergo apoptosis following withdrawal of IL-3 but is protected from cell death by overexpression of bcl-2. Nunez et al (1990) *J. Immunol.* 144: 3602–3610; and Hockenbery et al. (1990) *Nature* 348: 334–336. To assess the ability of Bak and Bak-2 to modulate apoptosis, cDNAs encoding Bak, Bak-2, two truncated forms of Bak (described below) and bcl-2 were ligated into the mammalian expression vector, pcDNA3 (Invitrogen, San Diego, Calif.) and stably introduced into the mouse progenitor B lymphocyte cell line FL5.12 by electroporation and selection in media containing the antibiotic G418. Assays were then performed on bulk transformants as described below.

The effects of the overexpressed genes on FL5.12 cell viability were examined at various times following withdrawal of IL-3. Cell viability was assessed by propidium iodide (PI) exclusion on a flow cytometer (Becton Dickinson FACScan). Bcl-2 expression protected the cells significantly from cell death while Bak appeared to enhance cell death when compared to the vector control. Bak-2 expression conferred a low level of protection from cell death at earlier times but was insignificant at later time points. Interestingly, BakΔ2 gave a moderate level of protection against cell death. Bak 1–112, a molecule that contains the N-terminal 112 amino acids of Bak, also appeared to partially protect the FL5.12 cells although at lower levels than Bcl-2.

Expression of Bak and BakΔ2 in WIL2 cells resulted in increased cell survival in response to anti-Fas-mediated apoptosis and serum withdrawal. Taken together, these data suggest that the various Bak molecules are capable of modulating apoptosis in a positive or negative manner, depending on the cell type and apoptotic stimuli. Thus, they are effective in preventing cell death such as in treperfusion tiic reperfusion tissue damage in the heart or in inducing cell death in cells that have escaped apoptotic control, as is the case in various cancers.

EXAMPLE 6

Bak interacts with Epstein-Barr Virus Encoded BHRF1 Protein

BHRF1 cDNA was amplified by RT-PCR from WIL2 mRNA using standard PCR protocol according to the instructions of the manufacturers of the PCR kit and thermal cycler (Perkin Elmer Cetus). The Flag-Bak and Flag-Bak-2 cDNAs were generated by RT-PCR as above from Bak and Bak-2/pcDNA3 plasmid templates but included the 24 base Flag encoding sequence 5'-GAC TAC AAG GAC GAC GAT GAC AAG-3' in the sense primer. This resulted in a cDNA encoding N-terminal Flag-Bak and Flag-Bak-2 fusion proteins that could be recognized and purified by the anti-Flag M2 antibody (Kodak-IBI). The cDNAs were ligated into the pcDNA3 vector which is under the control of the CMV and T7 RNA polymerase promoter. The Flag-Bak and BHRF1 plasmids or Flag-Bak-2 and BHRF1 plasmids were then cotranscribed and cotranslated using the TnT coupled reticulocyte lysate system according to manufacturers's instructions (Promega).

Briefly, 0.5–1.0 μg of the two circular plasmids were simultaneously transcribed and translated in 50 μL of TnT lysate for 90 minutes at 32° C. After translation, 20 μL of lysate was mixed with 20 μL of 2X PBS plus 40 μL of anti-Flag M2 affinity gel (Kodak) and incubated with gentle rocking overnight at 4° C. Immunoprecipitates were collected by centrifugation in an Eppendorf microfuge at 1500 rpm for 15 minutes at 4° C. Pellets were washed 4 times with 1.5 mL PBS and after the final wash were resuspended in 30 μL of SDS-PAGE sample buffer. The samples were then analyzed by SDS-PAGE on a 18% polyacrylamide gel. Gels were fixed with 10% glacial acetic acid, dried and exposed to X-ray film overnight at room temperature.

As shown in FIG. 3, Flag-Bak and BHRF1 as well as Flag-Bak-2 and BHRF1 were efficiently cotranscribed and cotranslated (lanes 1). Clearly, the anti-Flag M2 antibody could effectively coprecipitate Flag-Bak and BHRF1 or Flag-Bak-2 and BHRF1 (lanes 2). This demonstrates that BHRF1 interacts with both Bak and Bak-2 in vitro and suggests that such interactions occur in vivo resulting in the modulation of apoptosis. Interactions of BAK with viral proteins are likely to have evolved to allow viral replication or latency to proceed in the absence of apoptotic death of the host cell. Interference, therefore, in these interactions represents an important new strategy for the design of novel antiviral agents. Similarly, malignant cells derived from transformation by viruses such as EBV would also be amenable to diagnosis or therapy with these agents.

Although the foregoing invention has been described in some detail by way of illustration and example for purposes of clarity of understanding, it will be apparent to those skilled in the art that certain changes and modifications may be practiced. Therefore, the description and examples should not be construed as limiting the scope of the invention, which is delineated by the appended claims.

We claim:

1. An in vitro screening method to identify putative anti-viral therapeutic agents comprising the steps of:

(a) combining a Bak protein and a viral protein selected from the group consisting of BHRF-1 and E1B19K, under conditions in which binding between the two proteins occurs, to form a test sample;

(b) adding a putative therapeutic agent to the test sample of step (a); and (c) monitoring the effect of the putative therapeutic agent on the binding interaction between the Bak protein and viral protein, wherein disruption of this binding interaction, as compared to a control test sample lacking the putative therapeutic agent, indicates that said agent is a putative anti-viral therapeutic agent.

2. The method according to claim 1, wherein the viral protein is BHRF1.

3. The method according to claim 1, wherein the viral protein is E1B19K.

4. The method according to claim 1, wherein the potential therapeutic agent is selected from the group consisting of any pharmaceutical agent, cytokines, small molecule drugs, cell-permeable small molecule drugs, hormones, combinations of interleukins, lectins, and other stimulating agents including PMA, LPS, bispecific antibodies, peptide mimetics, antisense oligonucleotides and other agents which modify cellular functions or protein expression.

5. The method according to claim 1, wherein the Bak protein is selected from the group consisting of epitope-tagged Bak and epitope-tagged Bak-2.

6. The method according to claim 1, wherein the monitoring step is by a method selected from the group consisting of co-precipitation, protein interactive trapping, and enzyme linked immunosorbent assay (ELISA).

* * * * *